(12) United States Patent
Min et al.

(10) Patent No.: US 12,370,295 B2
(45) Date of Patent: Jul. 29, 2025

(54) THERAPEUTIC PLASMA EXCHANGE SYSTEMS AND METHODS

(71) Applicant: Fenwal, Inc., Lake Zurich, IL (US)

(72) Inventors: Kyungyoon Min, Kildeer, IL (US); Samantha Michalski Planas, Wauconda, IL (US)

(73) Assignee: Fenwal, Inc., Lake Zurich, IL (US)

( * ) Notice: Subject to any disclaimer, the term of this patent is extended or adjusted under 35 U.S.C. 154(b) by 1111 days.

(21) Appl. No.: 17/089,488

(22) Filed: Nov. 4, 2020

(65) Prior Publication Data

US 2021/0128811 A1    May 6, 2021

Related U.S. Application Data

(60) Provisional application No. 62/931,527, filed on Nov. 6, 2019.

(51) Int. Cl.
*A61M 1/34* (2006.01)
*A61K 38/38* (2006.01)
(Continued)

(52) U.S. Cl.
CPC ......... *A61M 1/3496* (2013.01); *A61K 38/385* (2013.01); *A61M 1/3441* (2013.01); *A61M 1/3455* (2013.01); *A61M 1/3616* (2014.02); *A61M 1/3621* (2013.01); *A61M 1/3626* (2013.01); *A61M 1/3633* (2013.01); *A61M 1/3663* (2013.01); *A61M 1/367* (2013.01); *A61M 1/3672* (2013.01); *A61M 1/3693* (2013.01); *A61M 1/38* (2013.01); *A61M 39/223* (2013.01); *A61M 1/265* (2014.02);
(Continued)

(58) Field of Classification Search
CPC .. A61M 1/265; A61M 1/3441; A61M 1/3455; A61M 1/3496; A61M 1/3621; A61M 1/3616; A61M 1/3626; A61M 1/3633; A61M 1/3663; A61M 1/3693; A61M 1/367; A61M 1/3672; A61M 1/38; A61M 39/223; A61M 2205/3393; A61M 2205/505; A61K 38/385
See application file for complete search history.

(56) References Cited

U.S. PATENT DOCUMENTS 4,954,128 A    9/1990    Ford
5,194,145 A    3/1993    Schoendorfer
(Continued)

FOREIGN PATENT DOCUMENTS

WO          9001970 A1       3/1990
WO       WO 90/01970   *    3/1990
(Continued)

OTHER PUBLICATIONS

Extended European Search Report and Written Opinion of Mar. 24, 2021, for European Application No. 20205593.5.
(Continued)

*Primary Examiner* — John Kim
(74) *Attorney, Agent, or Firm* — Cook Alex Ltd.

(57) ABSTRACT

Systems and methods for performing therapeutic plasma exchange are provided. The systems and methods utilize a plasmapheresis device that includes a controller that is configured and/or programmed to monitor the amount plasma collected and initiate delivery of a therapeutic agent.

18 Claims, 7 Drawing Sheets

(51) Int. Cl.
  *A61M 1/36* (2006.01)
  *A61M 1/38* (2006.01)
  *A61M 39/22* (2006.01)
  *A61M 1/26* (2006.01)

(52) U.S. Cl.
  CPC ............... *A61M 2205/3393* (2013.01); *A61M 2205/505* (2013.01)

(56) References Cited

U.S. PATENT DOCUMENTS

| | | | | |
|---|---|---|---|---|
| 5,200,090 | A | * | 4/1993 | Ford ................. A61M 5/16809 210/135 |
| 5,360,542 | A | | 11/1994 | Williamson, IV et al. |
| 2010/0168639 | A1 | | 7/2010 | Cantu |
| 2016/0089504 | A1 | | 3/2016 | Patel |
| 2018/0280603 | A1 | | 10/2018 | Fernandez |
| 2021/0008272 | A1 | * | 1/2021 | Patel ...................... G16H 10/60 |

FOREIGN PATENT DOCUMENTS

| | | | |
|---|---|---|---|
| WO | 9115253 | A2 | 10/1991 |
| WO | 2019226654 | A1 | 11/2019 |

OTHER PUBLICATIONS

Machine Translation of Japanese Search Report of May 23, 2024, for Japanese Application No. 2020-185047.

* cited by examiner

THERAPEUTIC PLASMA EXCHANGE SYSTEMS AND METHODS

CROSS-REFERENCE TO RELATED APPLICATION

This application claims the benefit of and priority to U.S. Provisional Patent Application Ser. No. 62/931,527, filed on Nov. 6, 2019, the disclosure of which is incorporated herein by reference in its entirety.

BACKGROUND

The present disclosure relates to systems and method for performing plasmapheresis and, more particularly, to Therapeutic Plasma Exchange. Even more particularly, the present disclosure relates to systems and methods for performing Therapeutic Plasma Exchange using an automated plasmapheresis device to remove plasma from a subject/patient and deliver one or more replacement fluids/therapeutic agents such as albumin.

Plasmapheresis is an apheresis procedure in which whole blood is withdrawn from a subject, the plasma is separated from the cellular blood components (red blood cells, platelets and leukocytes) and collected, and the cellular or formed blood components are returned to the subject. Therapeutic Plasma Exchange ("TPE") is a plasmapheresis procedure wherein plasma is separated, collected and discarded, and replaced with fresh frozen plasma or a solution that includes a plasma protein such as albumin. TPE is commonly used to treat several neurological and non-neurological conditions. The separation of the plasma from the cellular components is typically accomplished in an automated procedure by centrifugation or membrane filtration using a plasmapheresis device with a disposable fluid circuit mounted thereon, the disposable fluid circuit including one or more venipuncture needles that allow for access to the vascular system of the patient.

In TPE, whole blood is withdrawn from the subject/patient, mixed at a specified ratio with anticoagulant ("AC"), and then separated into anticoagulated plasma and red blood cells and other formed components. The separated plasma is collected in a plasma collection container while the formed components are returned to the patient. A replacement fluid that provides a therapeutic benefit as well as volume replacement is typically administered to the patient and often delivered with the formed components to replace lost blood volume and lost proteins. The withdrawal of plasma and reinfusion of the formed components with the infusion of a replacement fluid may occur concurrently where, for example, the disposable includes a venipuncture needle for withdrawal of the whole blood and a separate venipuncture for the return of formed components and infusion of the replacement fluid (a "dual" or "double needle" configuration). Alternatively, where a "single needle" configuration of the fluid circuit is used, the withdrawal of whole blood and reinfusion/replacement are alternated. As noted above, the replacement fluid may be fresh frozen plasma or a solution that includes albumin or other proteins and, if necessary, a further volume replacement fluid such as saline or other crystalloid solution.

The importance of TPE in the treatment of several diseases has prompted further efforts to develop systems, devices and methods that can efficiently and safely remove plasma from the patient and administer a desired amount of a replacement fluid/therapeutic agent.

SUMMARY

In one aspect, the present disclosure is directed to a plasmapheresis system for performing a therapeutic plasma exchange comprising a reusable hardware component and a disposable fluid circuit mounted thereon. The disposable fluid circuit includes a separator for separating whole blood into a plasma fraction and a formed component fraction, the separator having an input with a blood line integrally connected thereto for transporting whole blood from a subject to the separator. The separator includes a plasma output port integrally connected to a plasma collection container by a plasma line, and a formed component outlet port. The blood line terminates in a venipuncture needle for accessing the vascular system of the subject and withdrawing whole blood from the subject. An anticoagulant line is integrally connected to the blood line and configured to be connected to a source of anticoagulant for transporting anticoagulant to the blood line. A fluid replacement line is configured for delivering a replacement fluid/therapeutic agent to the subject, and a reinfusion line for transporting formed components to the subject is included.

The reusable hardware component includes a plurality of pumps for delivering anticoagulant at a controlled rate into the blood line during a collection phase, for delivering anticoagulated whole blood to the separator during the collection phase, for returning concentrated cellular components during a reinfusion phase, and for infusing a replacement fluid/therapeutic agent. The hardware component includes a programmable controller configured to monitor the amount of separated plasma collected and pause or terminate collection when a predetermined amount of plasma has been collected. The controller is also configured to initiate delivery of a predetermined amount of a replacement fluid/therapeutic agent through the fluid replacement line from a source after collecting the predetermined amount of plasma.

In another aspect, the present disclosure is directed to a method for performing a therapeutic plasma exchange in a plasmapheresis device that includes a disposable fluid circuit mounted on a reusable hardware component. The circuit includes a separation chamber, a venipuncture needle, a blood line in fluid communication with the venipuncture needle and an inlet of a separation chamber, a plasma product collection container in flow communication with an outlet on the separation chamber, and a fluid replacement line in flow communication with a source of a replacement fluid/therapeutic agent. The method includes withdrawing whole blood from a subject and introducing anticoagulated whole blood into the separation chamber, separating the whole blood into a plasma product and formed components. The method further includes collecting a predetermined amount of plasma product in a plasma product container, returning the formed components to the subject, and delivering an amount of a replacement fluid/therapeutic agent through the replacement fluid line to the subject when the predetermined amount of plasma product has been collected in the plasma collection container.

In another aspect, the present disclosure is directed to a method for performing a therapeutic plasma exchange in a plasmapheresis device including a disposable fluid circuit mounted on a reusable hardware component. The circuit includes a separation chamber, a venipuncture needle, a blood line in fluid communication with the venipuncture needle and an inlet of a separation chamber, a plasma product collection container in flow communication with an outlet on said separation, and a replacement fluid line in flow communication with a source of a replacement fluid/therapeutic agent. The method further includes withdrawing whole blood from a subject and introducing anticoagulated whole blood into the separation chamber, separating the whole blood into a plasma product and formed components, and collecting the plasma product in a plasma product container. Further, the method includes returning the formed components to the subject and delivering an amount of a replacement fluid/therapeutic agent through the replacement fluid line to the subject when a predetermined amount of plasma product has been collected in the plasma collection container. In accordance with one aspect of the method disclosed herein, the infusion of the amount of replacement fluid/therapeutic agent delivered to the subject is monitored.

DETAILED DESCRIPTION

A more detailed description of the systems and methods in accordance with the present disclosure is set forth below. It should be understood that the description below of specific devices and methods is intended to be exemplary, and not exhaustive of all possible variations or applications. Thus, the scope of the disclosure is not intended to be limiting, and should be understood to encompass variations or embodiments that would occur to persons of ordinary skill.

In the context of the present application, therapeutic plasmapheresis and, more particularly TPE is performed on an automated system comprising a hardware component, generally designated 10, and a disposable set or fluid circuit, generally designated 12 (FIG. 3), to collect plasma from a subject/patient. With reference to FIGS. 1-5 and 7, and as described in greater detail below, the disposable fluid circuit 12 includes an integrally connected separator, containers, and tubing to transport blood and solutions within a sterile fluid pathway.

Figure 2:
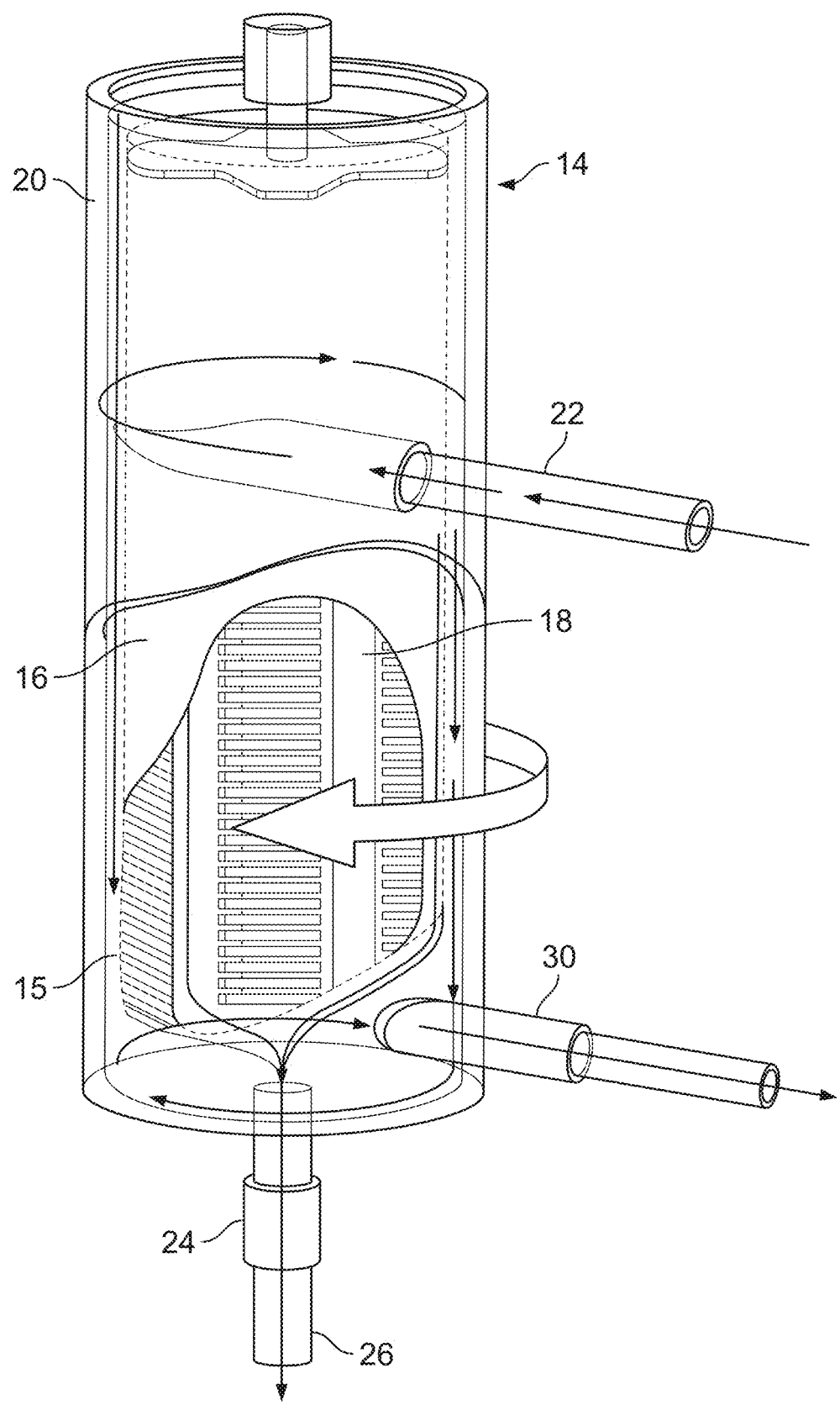
FIG. 2 is a perspective view of a spinning membrane separator of the type incorporated in a disposable set, with portions broken away to show detail, usable with the TPE system of FIG. 1.
Figure 3:
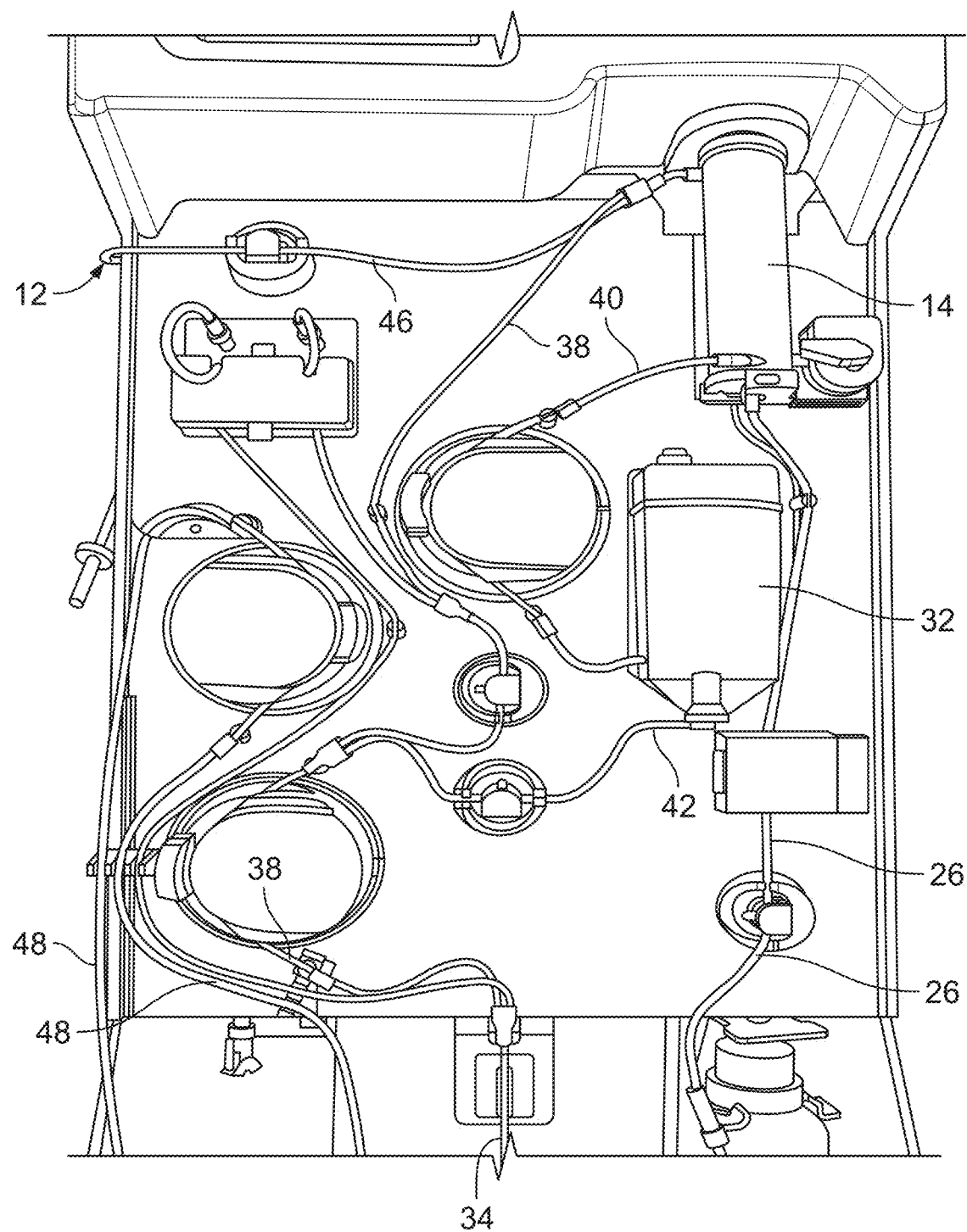
FIG. 3 is a perspective view of one embodiment of the front panel of the TPE system of FIG. 1, showing the components of the disposable fluid circuit that are mounted thereon.

The separator 14, best seen in FIG. 2, may be a spinning membrane filter 16 mounted to a rotor 18 for rotation within a case 20 to separate blood into components. Separator 14 includes a gap or separation chamber 15 between rotor 18 and the inner wall of case 20. A detailed description of a spinning membrane separator may be found in U.S. Pat. No. 5,194,145 to Schoendorfer, which is incorporated herein by reference. As can be appreciated, in a different system, separation of the whole blood may be accomplished by centrifugation. See, e.g. U.S. Pat. No. 5,360,542 to Williamson et al.

Figure 4:
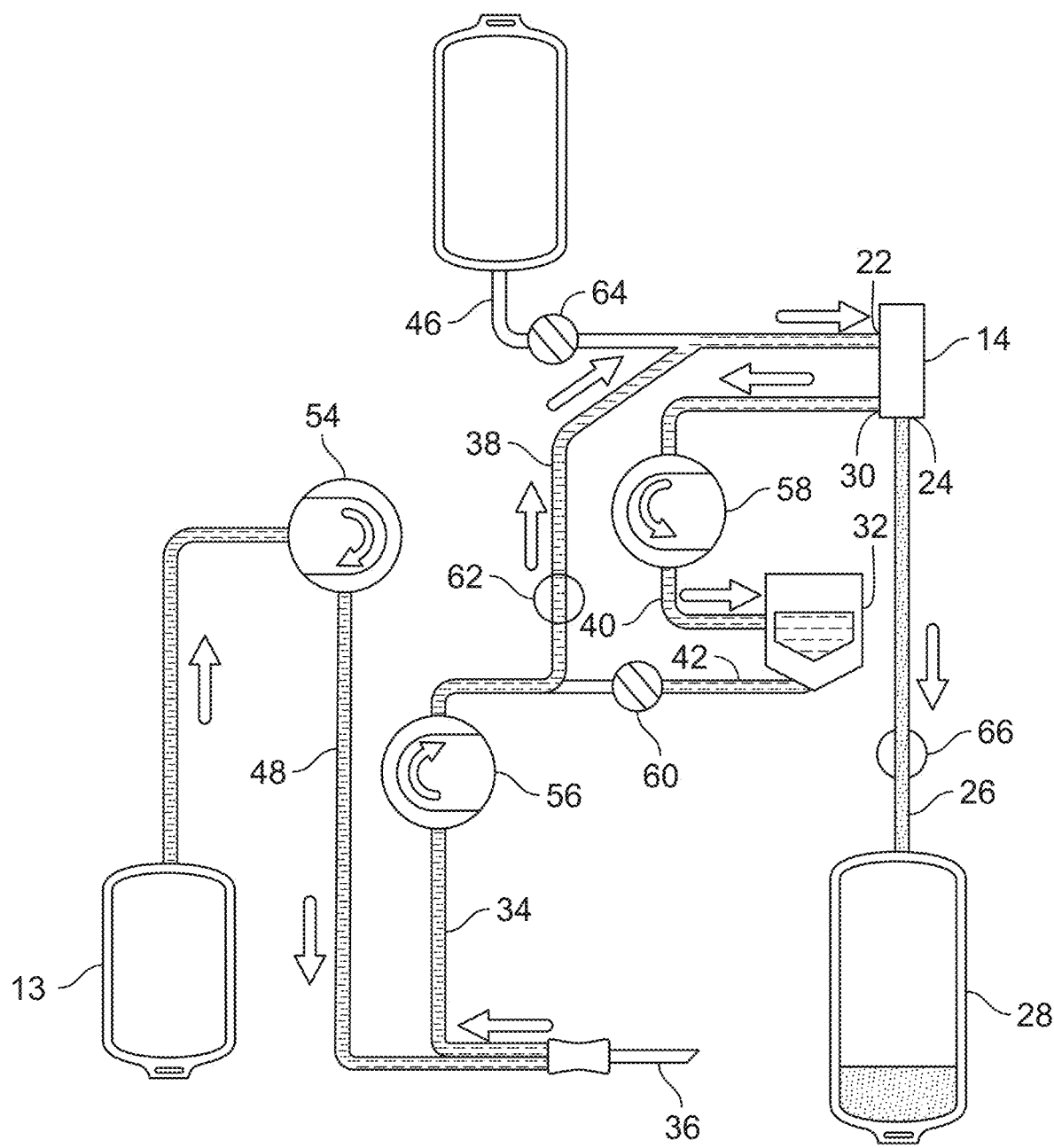
FIG. 4 is a schematic view showing operation of the TPE system in the collection phase of a TPE procedure.
Figure 5:
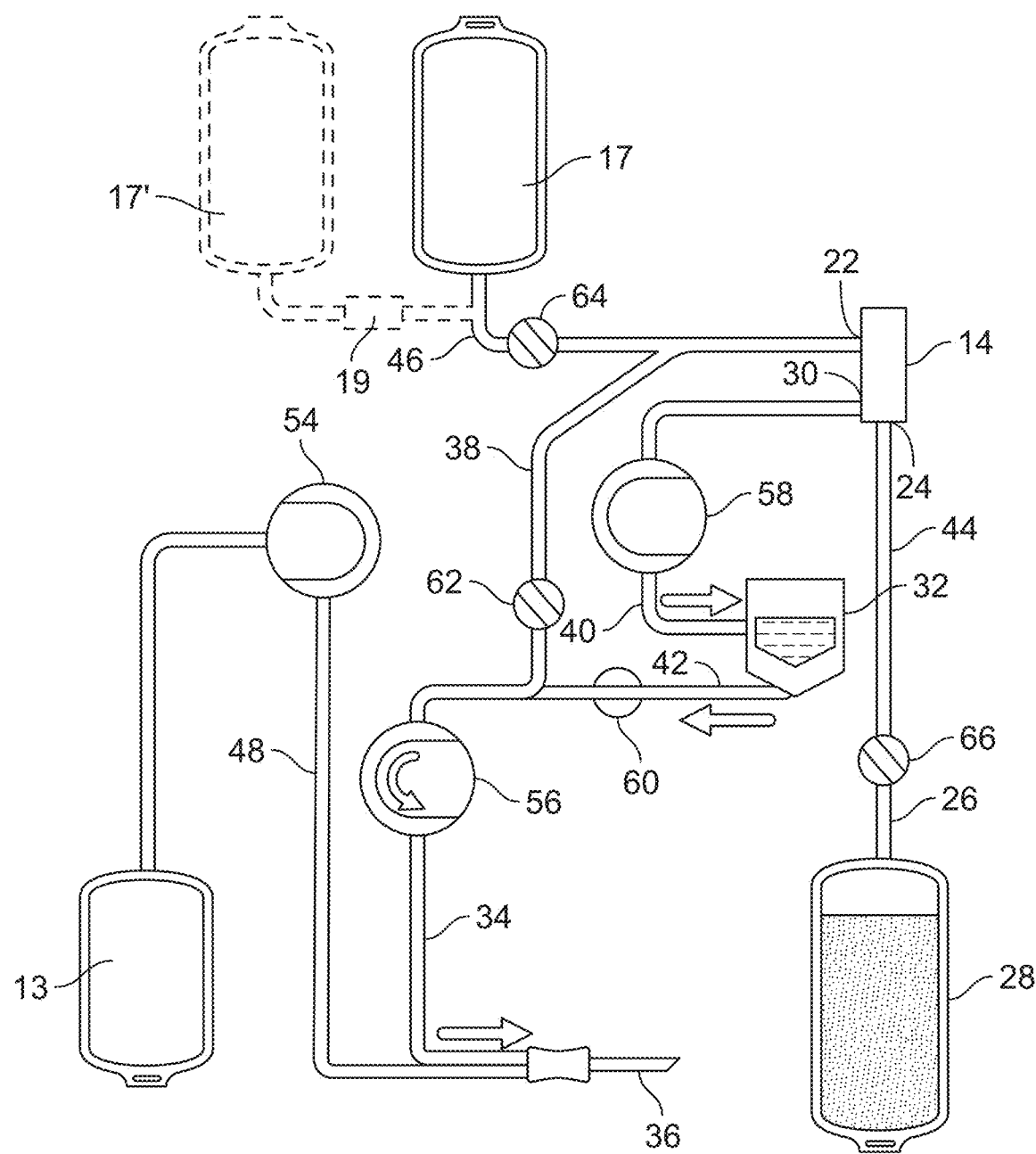
FIG. 5 is a schematic view showing operation of the TPE system in the reinfusion and the replacement phases of a TPE procedure.
Figure 7:
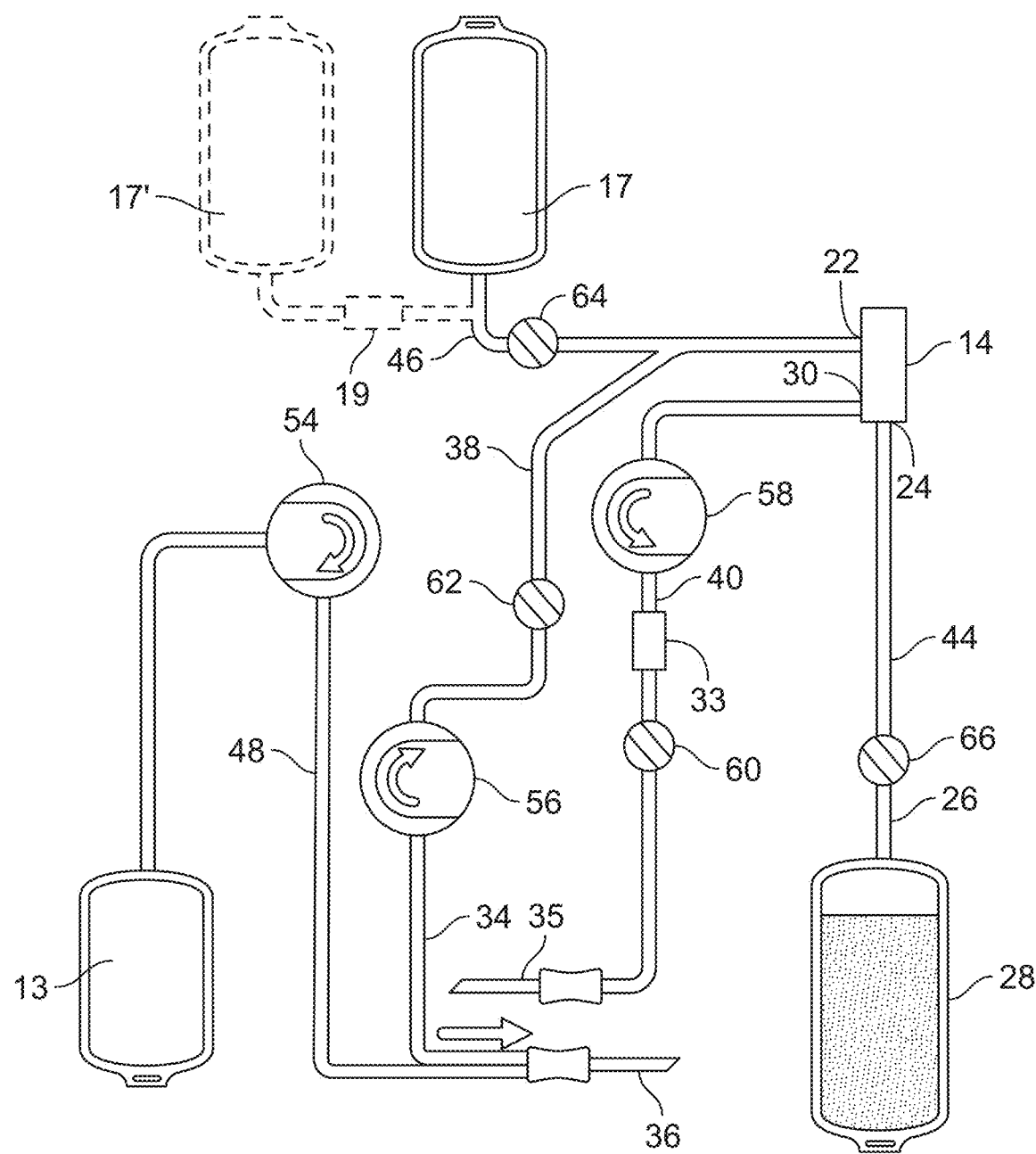
FIG. 7 is a schematic view showing a dual-needle TPE system.

During TPE, whole blood is withdrawn from a patient through a patient access device 36, such as a venipuncture needle (shown in FIGS. 4 and 5). The entering whole blood is combined, at a selected ratio of whole blood to anticoagulant, with anticoagulant from container 13 at a junction of whole blood line 34 and anticoagulant line 48. Anticoagulated whole blood enters the separator 14 through a whole blood input port 22. The plasma is separated by the spinning membrane filter and then passes out of a plasma output port 24, through a plasma line 26, and into a plasma collection container 28. In a single needle configuration, depicted in FIG. 4, concentrated cells are pumped out of the separation chamber, through formed component output port 30 into a reservoir 32, where the cells remain until reinfusion to the patient. Where a dual needle configuration of the fluid circuit is used, as shown in FIG. 7, the separated formed components are pumped out of the separation chamber (without residing in a reservoir) and reinfused to the patient.

The disposable fluid circuit 12 also includes tubing lines defining flow paths for (1) introducing whole blood from the patient into the system during collection and returning formed cells to the patient during reinfusion (whole blood line 34, which terminates in the venipuncture needle 36, (or in a double needle configuration, needle 35 of FIG. 7), and for (2) transporting anticoagulated whole blood to the separator (blood line 38), concentrated cells into the reservoir (cell line 40), (3) for transporting concentrated cells from the reservoir to the blood line in a single needle configuration (reinfusion line 42), (4) flowing plasma into the plasma collection container (plasma line 44), and (5) infusing a replacement fluid including a therapeutic agent and/or a therapeutic drug (replacement fluid line 46), and (6) delivering an anticoagulant (AC line 48) to the whole blood.

The hardware component 10 includes a programmable controller 50 and touch screen 52 with a graphical user interface ("GUI") through which the operator controls the procedure. For example, the GUI permits entry of any of a patient ID, patient sex, patient height, patient weight, patient age, patient hematocrit/hemoglobin; a target replacement fluid infusion volume, and a target plasma volume. The touch screen 52 also enables the operator to gather status information and handle error conditions.

Typically, hardware component 10 will include a plurality of pumps for transporting whole blood, separated and formed components, replacement fluids including therapeutic agents and/or therapeutic drugs and anticoagulant through the fluid circuit. In one embodiment, three (3) pumps are located on the front panel of the hardware component 10, including an AC pump 54, a blood pump 56, and a cell pump 58. As further shown in the Figures, the pumps are peristaltic pumps. The AC pump 54 delivers anticoagulant solution (AC) at a controlled rate into the blood line 34 as whole blood enters the circuit from the patient. The blood pump 56 delivers anticoagulated whole blood to the separator during the collection phase of the procedure and returns concentrated cellular components and replacement fluid to the patient during the replacement phase of the procedure. The cell pump 58 delivers formed or cellular components and replacement fluid(s)/therapeutic agents and/or therapeutic drugs from the separator 14 to a reservoir during the collection phase or to the patient during a reinfusion phase as shown in the double needle configuration of FIG. 7.

The front panel will also typically include a plurality of flow control devices to selectively open and close flow paths, as necessary, during the TPE procedure. As shown in the Figures, in one embodiment, hardware component 10 includes four clamps into which the tubing segments of disposable circuit 12 are installed, including a reinfusion clamp 60, a blood clamp 62, a replacement fluid clamp 64, and a plasma clamp 66. The reinfusion clamp 60 closes to block the reinfusion line (42) during the collection phase and is open during the reinfusion phase to reinfuse the formed components (from the reservoir 32 in a single needle configuration) to the subject/patient. The blood clamp 62 opens during the collection phase to allow anticoagulated whole blood to be pumped to the separator 14 and closes during the reinfusion phase to block the blood line 38. The replacement fluid clamp 64 closes to block the replacement fluid line 46 during the collection phase and opens during the infusion of the replacement fluid and/or therapeutic agent and/or drug. The plasma clamp 66 opens during the collection phase to allow plasma to flow into the plasma collection container 28 and closes during the reinfusion phase.

As with the pumps and clamps described above, hardware component 10 may include one or more weigh scales from which containers of source fluids and fluids to be collected may be suspended. Weigh scales may be associated with or include weight sensors to monitor the delivery and collection of fluids. For example, as shown in the Figures, hardware component 10 may include a plurality of weigh scales to monitor the amounts of the fluids being delivered or collected such as the plasma collection volume (scale 68), the AC solution volume (scale 70), and the formed component volume (scale 72). In other embodiments, a single weigh scale may be provided on the hardware component from which one or more containers may be suspended, as needed or desired. As described below, scales 68, 70 or 72 may also be used to monitor fluid amounts in other containers used to during the TPE procedure. The system may also include additional sensors and detectors, including a venous pressure sensor 74, a separator pressure sensor 76, optical blood detectors 78, and an air detector 80. The pumps, clamps, weigh scales and other detectors communicate with programmable controller 50 as will now be described.

Figure 6:
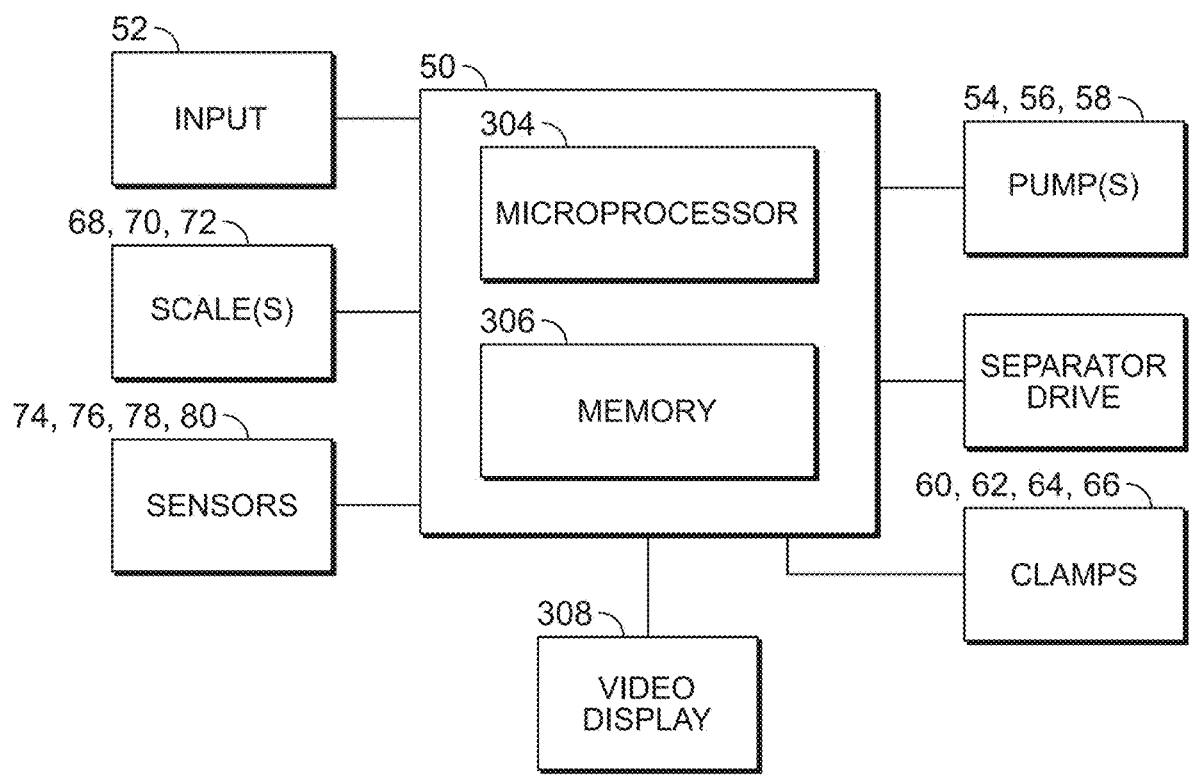
FIG. 6 is a schematic view of the control circuitry, including the controller, of the device of FIGS. 1-3.

FIG. 6 is a schematic view of the control unit or "controller" 50 included in hardware component 10. The controller 50 may include a microprocessor 304 (which may include multiple physical and/or virtual processors). According to other embodiments, the controller 50 may include one or more electrical circuits designed to carry out the actions described herein. In an embodiment, controller 50 may include a microprocessor and other circuits or circuitry. In addition, the controller 50 may include one or more memories 306. The instructions by which the microprocessor 304 is programmed may be stored on the memory 306 associated with the microprocessor 304, which memory/memories 306 may include one or more tangible non-transitory computer readable memories, having computer executable instructions stored thereon, which when executed by the microprocessor 304 may cause the microprocessors 304 to carry out one or more actions as described herein.

As is also illustrated in FIG. 6, controller 50 may be coupled to one or more of the structures described above, for example, to receive information (e.g., in the form of signals) from these structures or to provide commands (e.g., in the form of signals) to these structures to control the operation of the structures. As illustrated in FIG. 6, the controller 50 may be coupled to the one or more scales 68, 70 and 72 (seen in FIG. 3) that hold solution containers or containers provided to collect blood components, the sensors associated with clamps 60, 62, 64 and 66 and at least one input 52 to receive information from those devices. Additionally, the controller 50 may be coupled to pumps 54, 56 and 58 and the drive unit for separator 14 to provide commands to those devices and to control their operation. It may also be possible that the controller 50 receives information from and provides commands to a given structure, such as one of the structures already mentioned. The controller 50 may be directly electrically connected to these structures to be coupled to them, or the controller 50 may be directly connected to other intermediate equipment that is directly connected to these structures to be coupled to them. Controller 50 may also calculate or estimate values (such as flow rates, infusion volumes, and the like), in response to data entered by the operator and/or signals or other information received from the structures described above.

The at least one input 52 may include a number of different devices according to the embodiments described herein. For example, the input 52 could include a keyboard or keypad by which a user may provide information and/or instructions to the controller 50. Alternatively, the input 52 may be a touch screen, such as may be used in conjunction with a video display 308 that is disposed on the front panel of hardware component 10, the video display 308 also being coupled to the controller 50. The assembly of the input/touch screen 52 and video display 308 may be one of the aforementioned structures to which the controller 50 is coupled from which the controller 50 receives information and to which the controller 50 provides commands.

In accordance with the TPE methods described herein, the patient is connected to the system throughout the procedure. As illustrated in FIGS. 4 and 5, the disposable fluid circuit 12 includes a single venipuncture needle 36, through which whole blood is drawn from the donor in a collection phase (FIG. 4) and concentrated cells are returned to the donor in a reinfusion stage (FIG. 5) and the replacement fluid/therapeutic agent and/or a therapeutic drug is infused during the replacement phase. However, it will be understood that a "dual-needle" circuit wherein whole blood is withdrawn from the patient through a first venipuncture needle while formed components and replacement fluid, including therapeutic agents and/or therapeutic drugs are infused through a second venipuncture needle. FIG. 7 shows a dual-needle option with the second venipuncture 35 needle.

At least a portion of a TPE procedure in accordance with the present disclosure and using a single needle configuration may be carried out in a plurality of cycles, each cycle having a collection/separation phase followed by a reinfusion phase. Once all cycles of collection/separation and reinfusion have been completed, the method further includes a replacement phase wherein a replacement fluid/therapeutic agent is delivered to the patient. During the collection phase, the whole blood is separated into plasma and concentrated cells. As described above, the disposable fluid circuit includes a plasma collection container 28 for receipt of the separated plasma and a reservoir 32 for receipt of the formed components. During the reinfusion phase, the formed cells from the reservoir 32 are reinfused to the patient through the venipuncture needle 36 in a "single needle" TPE procedure. Typically, TPE performed with a single venipuncture needle 36 involves multiple cycles of collection and reinfusion where a partial collection of the plasma to be collected is alternated with a reinfusion phase wherein formed components that have been collected in reservoir 32 are returned. The cycles are repeated until the predetermined amount of plasma product has been collected.

Returning to FIG. 4, during the collection phase, anticoagulant solution (AC) is pumped at a controlled rate and mixed with whole blood as it enters the disposable set 12. The anticoagulated blood is pumped to the separator 14, where plasma is separated from the formed components and directed to the plasma collection container 28. The formed components are pumped from the separator 14 to the reservoir 32. The collection phase stops when the reservoir 32 reaches an expected amount of concentrated cells or, as noted above, if the predetermined target plasma collection volume has been achieved.

Once all of the collection/separation and reinfusion cycles have been completed, the replacement phase may begin. The replacement phase includes infusion of the replacement fluid/therapeutic agent from container 17. The replacement fluid/therapeutic agent is pumped from container 17 by pump 58 in response to a command from controller 50 and/or by blood pump 56 (in a reverse direction) as shown in FIG. 5 In a single needle embodiment, as shown in FIG. 5, the replacement fluid/therapeutic agent is pumped from container(s) 17 (17'), through fluid replacement line 46, though separator 14, reservoir 32, reinfusion line 42, blood line 34 through venipuncture needle 36, to the patient. Alternatively, the replacement fluid/therapeutic agent may be pumped (by pump 56) through line 38 and blood line 34, and venipuncture needle 36 to the patient.

In a dual needle embodiment, of the type shown in FIG. 7, the replacement fluid/therapeutic agent is pumped from container(s) 17(17'), through fluid replacement line 46, though separator 14, air trap 33 (in lieu of reservoir 32), and return needle 35 to the patient. In a dual-needle procedure, the collection and reinfusion phases are concurrent.

As indicated above, the replacement fluid/therapeutic agent for TPE procedures may be plasma such as fresh frozen plasma or an albumin solution which replaces lost volume and provides a therapeutic benefit to the patient. As described below, the replacement fluid/therapeutic agent may also include saline which likewise serves to replace lost volume and may also have a beneficial therapeutic effect. Container 17 of a replacement fluid/therapeutic agent may be pre-attached to fluid circuit 12 or, more typically, attached to circuit 12 at the time of use. Container 17 may be suspended from an independent, standard IV pole or from a hook on hardware component 10.

The amount of replacement fluid/therapeutic agent administered to the patient may be monitored by the number of pump rotations or pump strokes of pump 56 or 58. Once a predetermined amount of replacement fluid/therapeutic agent has been delivered to the patient, pumping will terminate.

In an alternative embodiment, the amount of replacement fluid administered to the patient may be monitored by sensing the change in weight (and thus, the volume) of container 17 during the infusion of the replacement fluid/therapeutic agent portion of the replacement phase. In this embodiment, the method includes removing container 17 from the IV pole or hook and suspending it from a weigh scale or from one of the plurality of available weigh scales 68, 70 or 72 just prior to commencement of the replacement phase. For example, once the predetermined (partial or total) target volume of plasma is collected, weigh scale 68 will send a signal to the controller 50 that plasma collection is complete. Upon receiving an indication or prompt, the operator may remove plasma container 28 from weigh scale 68 and move the replacement fluid/therapeutic agent container 17 from the IV pole/hook and place it on weigh scale 68. Weigh scale now monitors the infusion of the replacement fluid/therapeutic agent in container 17 until a predetermined amount of the replacement fluid/therapeutic agent is delivered to the patient. Of course, it will be understood that other available weigh scales (70, 72) may be used in lieu of weigh scale 68.

Figure 1:
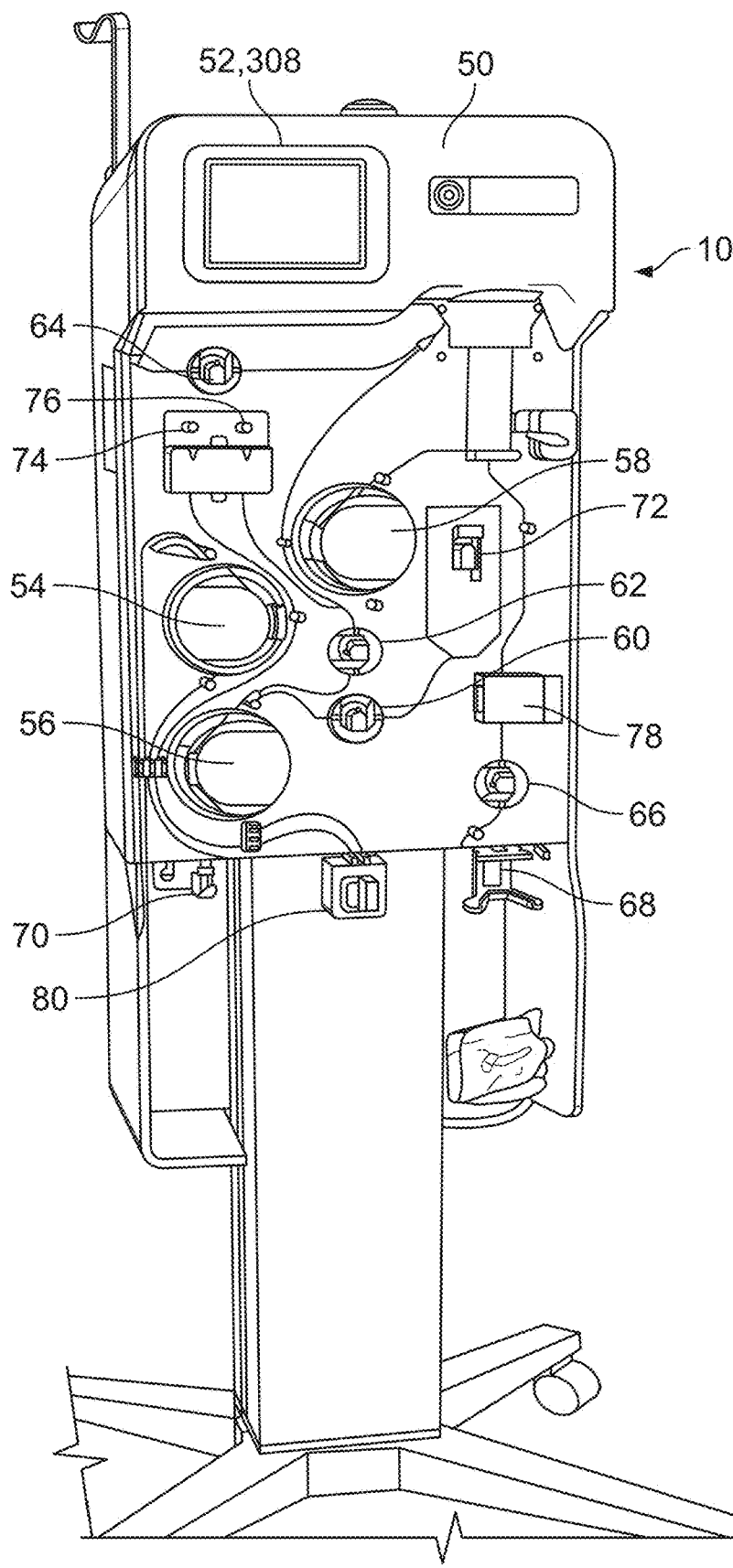
FIG. 1 is a perspective view of an exemplary plasmapheresis instrument suitable for use in the TPE systems and methods of the present application.

In a further alternative embodiment of monitoring the amount of replacement fluid delivered to the patient, container 17 may include a fixed amount of replacement fluid/therapeutic agent, all of which is to be delivered to the patient. In this embodiment, replacement fluid line 46 may be associated with a detector, such as air detector 80 (FIG. 1). Infusion of the replacement fluid/therapeutic agent continues until detector 80 senses the presence of air in line 46, sending a signal to controller 50 which ceases rotation of pump 56 or 58, thereby ceasing delivery of the replacement fluid/therapeutic agent.

The volume of replacement fluid/therapeutic agent required or desired may vary from patient to patient. For example, in some embodiments, the volume may be a fixed amount that is entered by the operator using the user interface. Once entered, the controller will continue the infusion of replacement fluid/therapeutic agent has reached the entered target volume.

In another embodiment, the volume of replacement fluid/therapeutic agent delivered may be calculated by the controller as a percentage of the total volume of plasma product or raw plasma collected from the patient. For example, the controller may be pre-programmed to collect 25% (or some other percentage) of the actual or raw plasma collected from the donor. As part of the replacement fluid/therapeutic agent infusion, the amount of raw plasma that can be safely removed from the patient must be determined. Inasmuch as the volume of plasma product collected in plasma container 28 includes both plasma and some amount of anticoagulant, the controller calculates the amount of plasma in the collected plasma product and whether such amount matches the targeted amount of plasma product. Once the predetermined targeted amount of plasma has been reached (as measured by weigh scale 68) and formed components have been reinfused, plasma collection may stop and infusion of the replacement fluid/therapeutic agent as a pre-determined percentage of the collected plasma may commence, all under the direction of the controller.

Occasionally, plasma collection may need to be terminated prior to collection of the targeted and originally determined or desired amount of plasma due to, for example, the condition of the patient or a device malfunction. In such cases, the system determines the amount of plasma actually collected and adjusts the volume of replacement fluid/therapeutic agent to be delivered to the patient as a percentage of the actual plasma collected. For example, where a desired or an originally determined volume of plasma available for collection is 800 ml but only 600 ml is collected, the system will adjust the amount of replacement fluid/therapeutic agent to the selected percentage or ratio of plasma to replacement fluid/therapeutic agent. Thus, continuing with the present example wherein only 600 ml of a desired 800 ml is collected and where the percentage of replacement fluid/therapeutic agent was selected to be 25% of the plasma volume removed from the patient, the controller will adjust the amount of replacement fluid/therapeutic agent to be delivered from 200 ml to 150 ml.

In another aspect, the system can be configured or programmed to deliver the replacement fluid/therapeutic agent incrementally or partially to the patient. Once the amount of the replacement fluid/therapeutic agent to be delivered has been determined, infusion may proceed in increments or as a percentage of the total volume that is to be delivered. Thus, a portion of the replacement fluid/therapeutic agent may be delivered at one point of the procedure and the remainder delivered at other points of the procedure. Infusion of the replacement fluid/therapeutic agent incrementally may, in one alternative embodiment, be performed as part of the collection/separation and reinfusion cycles to protect against an excess fluid volume deficit during the TPE procedure.

In still a further aspect, the system may be configured or programmed to deliver more than one replacement fluid and/or therapeutic agent using the same plasmapheresis device. Disposable fluid circuit 12 may be provided with separate containers of different replacement fluids and/or therapeutic agents, each in fluid communication with replacement fluid line 46, as shown in FIG. 5 (in broken lines). The controller may be programmed to selectively open and close clamps and thereby flow paths 17 and 17' to allow flow of the two (or more) fluids. Alternatively, containers 17 and 17' may be joined by a (three-way) valve 19 that, under the direction of the controller can open and close to selectively allow and block flow from the containers. In an embodiment, an albumin solution may be the first fluid (in container 17) and saline may be a second fluid (in container 17') with the controller programmed to infuse albumin at one point of the TPE procedure and saline at another point of the TPE procedure.

The volume of replacement fluid/therapeutic agent to be delivered to the patient can be established by established protocols or, in accordance with the systems and methods disclosed herein, can be tailored to the patient undergoing TPE. As described above, in one embodiment, the volume of replacement fluid/therapeutic agent can be a pre-programmed percentage of the plasma available for collection from the patient or the total plasma product to be collected. The plasma available for collection and/or the total plasma product to be collected may be determined by pre-programmed nomograms similar to those described with respect to certain plasmapheresis (plasma collection) protocols in International Application No. PCT/US19/33318, filed May 21, 2019, the contents of which are incorporated herein by reference. As described in this referenced International Application, the plasma available for collection and/or the total plasma product to be collected may be based on certain parameters of the subject undergoing plasmapheresis such as, but not limited to, the total plasma volume of the subject, hematocrit and further based on the height, weight, sex, age of the subject patient. Thus, the system, under the direction of the controller may receive patient data of the type described above and calculate the amount of plasma that can be safely collected from a given patient based on pre-programmed nomograms. Once the controller has calculated the amount of plasma that can be collected and/or the predetermined target plasma volume, the controller may calculate/estimate the volume of replacement fluid/therapeutic agent required for infusion, whether as a percentage of the calculated plasma volumes, or based on other factors.

Alternatively, the volume of replacement fluid/therapeutic agent to be delivered to the patient may be calculated or estimated more directly on the patient parameters. In that regard, the controller may be pre-programmed with one or more nomograms that will estimate or calculate the volume of replacement fluid/therapeutic agent to be infused based on one or more or two or more donor characteristics including hematocrit and, more particularly the height, weight, sex, age of the patient.

OTHER EXAMPLES

Aspect 1. A plasmapheresis system for performing a therapeutic plasma exchange comprising a reusable hardware component and a disposable fluid circuit: the disposable fluid circuit comprising i) a separator for separating whole blood into a plasma fraction and a formed component fraction, the separator having an input having a blood line integrally connected thereto for transporting whole blood from a subject to the separator, a plasma output port integrally connected to a plasma collection container by a plasma line, and a formed component outlet port; ii) said blood line terminating in a venipuncture needle for transporting whole blood from a subject to the blood line, iii) an anticoagulant line integrally connected to the blood line and configured to be connected to a source of anticoagulant for transporting anticoagulant to the blood line, iv) a fluid replacement line configured for delivering a replacement fluid/therapeutic agent to the subject, and v) a reinfusion line for transporting formed components to said subject; (a) the reusable hardware component comprising a plurality of pumps for delivering anticoagulant at a controlled rate into the blood line during a collection phase, anticoagulated whole blood to the separator during the collection phase and for returning concentrated cellular components during a reinfusion phase, concentrated cellular components from the separator and infusing a replacement fluid/therapeutic agent and a programmable controller configured to (i) monitor the amount of separated plasma collected and pause or terminate collection when a predetermined amount of plasma has been collected; and (ii) initiate delivery of a predetermined amount of a replacement fluid/therapeutic agent through the fluid replacement line from a source after collecting said predetermined amount of plasma.

Aspect 2. The system of Aspect 1 wherein said therapeutic agent comprises albumin.

Aspect 3. The system of any one of Aspects 1 through 2 wherein said fluid circuit further comprises a reservoir integrally connected to said formed component port of said separator.

Aspect 4. The system of any one of Aspects 1 and 2 wherein said disposable fluid circuit comprises a first venipuncture needle for transporting whole blood from a subject and a second venipuncture needle for returning said formed components and delivering said replacement fluid/therapeutic agent to said subject.

Aspect 5. The system of any one of Aspects 1 through 3 wherein the hardware component comprises one or more weigh scales configured to receive a source of replacement fluid/therapeutic agent.

Aspect 6. The system of any one of Aspects 1 through 4 wherein said fluid replacement line is in openable flow communication with said reinfusion line.

Aspect 7. The system of Aspect 5 wherein said reinfusion line is in flow communication with said blood line and said venipuncture needle.

Aspect 8. The system of Aspect 4 wherein said fluid replacement line is in flow communication with said second venipuncture needle.

Aspect 9. A method for performing a therapeutic plasma exchange in a plasmapheresis device comprising a disposable fluid circuit mounted on a reusable hardware component, said circuit including a separation chamber, a venipuncture needle, a blood line in fluid communication with said venipuncture needle and an inlet of a separation chamber, a plasma product collection container in flow communication with an outlet on said separation chamber, and a replacement fluid line in flow communication with a source of a replacement fluid/therapeutic agent, said method comprising: a) withdrawing whole blood from a subject and introducing anticoagulated whole blood into said separation chamber; b) separating said whole blood into a plasma product and formed components; c) collecting a predetermined amount of said plasma product in a plasma product container; d) returning said formed components to said subject; and e) delivering an amount of a replacement fluid/therapeutic agent through said replacement fluid line to said subject when said predetermined amount of plasma product has been collected in said plasma collection container.

Aspect 10. The system of any one of Aspects 1 through 8 wherein said controller is further configured to monitor the amount of said replacement fluid/therapeutic agent delivered to said subject.

Aspect 11. The system of any one of Aspects 1 through 8 further comprising a sensor that sends a signal to the controller when a predetermined amount of said replacement fluid/therapeutic agent has been delivered to said subject.

Aspect 12. The system of any one of Aspects 1 through 8 further comprising a sensor that sends a signal to the controller when said infusion of said replacement fluid/therapeutic agent is complete.

Aspect 13. The system of any one of Aspects 1 through 8 wherein said controller is further configured to calculate an amount of replacement fluid/therapeutic agent delivered to said subject wherein said amount of therapeutic agent delivered is based on a percentage of collected plasma/therapeutic agent.

Aspect 14. The system of Aspect 13 wherein said controller is further configured to pause or terminate said infusion of said replacement fluid/therapeutic agent when said amount of replacement fluid/therapeutic agent based on said ratio of collected plasma/therapeutic agent is delivered to said subject.

Aspect 15. The system of any one of Aspects 1 through 8 and 10 through 14 wherein said amount of said replacement fluid/therapeutic agent is a fraction of a total volume of said therapeutic agent to be delivered and said controller is further configured to pause said infusion of therapeutic agent when said fraction has been delivered to said subject.

Aspect 16. The system of any one of Aspects 1 through 8 and 10 through 15 wherein said disposable kit comprises both a container of volume replacement fluid and a container of said therapeutic agent.

Aspect 17. The system of Aspect 16 wherein said container of volume replacement fluid and a container of said therapeutic agent are in openable flow communication with said replacement fluid line.

Aspect 18. The system of Aspect 17 further comprising one or more flow controllers for establishing flow of said volume replacement fluid through said replacement fluid line while preventing flow of said therapeutic agent through said replacement line.

Aspect 19. The system of Aspect 18 wherein said one or more flow controllers comprises a three-way valve.

Aspect 20. The system of any one of Aspects 1 through 8 and 10 through 19 wherein said controller is configured to calculate a target volume of plasma to be collected based on at least two of the height, weight, sex, age and hematocrit of said subject.

Aspect 21. The system of Aspect 20 wherein the controller is configured to calculate the amount of said treating agent to be delivered based on said calculated target volume of plasma to be collected.

Aspect 22. The system of any one of Aspects 1 through 8 and 10 through 21 comprising a reservoir in flow communication with a second outlet on said separation chamber for receiving the separated formed components.

Aspect 23. The system of any one of Aspects 1 through 8 and 10 through 21 wherein said disposable fluid circuit comprises a first venipuncture needle for transporting whole blood from a subject and a second venipuncture needle for returning said formed components and delivering said replacement fluid/therapeutic agent to said subject.

Aspect 24. A method for performing a therapeutic plasma exchange in a plasmapheresis device comprising a disposable fluid circuit mounted on a reusable hardware component, said circuit including a separation chamber, a venipuncture needle, a blood line in fluid communication with said venipuncture needle and an inlet of a separation chamber, a plasma product collection container in flow communication with an outlet on said separation chamber, and a replacement fluid line in flow communication with a source of a replacement fluid/therapeutic agent, said method comprising: a) withdrawing whole blood from a subject and introducing anticoagulated whole blood into said separation chamber; b) separating said whole blood into a plasma product and formed components; c) collecting said plasma product in a plasma product container; d) returning said formed components to said subject; e) delivering an amount of a replacement fluid/therapeutic agent through said replacement fluid line to said subject when said predetermined amount of plasma product has been collected in said plasma collection container and f) monitoring the infusion of said amount of said replacement fluid/therapeutic agent delivered to said subject.

Aspect 25. The method of Aspect 24 comprising monitoring said amount of said replacement fluid/therapeutic agent delivered by suspending a container of said replacement fluid/therapeutic agent from a weigh scale of said reusable hardware component.

Aspect 26. The method of any one of Aspects 24 through 25 wherein said monitoring comprises detecting for the presence of air in the replacement fluid line during said delivering.

Aspect 27. The method of any one of Aspects 24 through 26 comprising withdrawing whole blood through said venipuncture needle and delivering said replacement fluid/therapeutic agent through said venipuncture needle.

Aspect 28. The method of any one of Aspects 24 through 27 comprising collecting said formed components in said reservoir.

Aspect 29. The method of any one of Aspects 24 through 28 comprising determining the amount of replacement fluid/therapeutic agent to be delivered to said subject.

Aspect 30. The method of Aspect 29 comprising determining the amount of said replacement fluid/therapeutic agent to be delivered to the subject based on the predetermined amount of plasma product to be collected.

Aspect 31. The method of Aspect 29 comprising determining the amount of said therapeutic agent to be delivered based on the amount of plasma product collected in said plasma container.

Aspect 32. The method of any one of Aspects 24 through 31 wherein said predetermined amount of plasma is based on at least two of the height, weight, sex and hematocrit of said subject.

Aspects 33. The method of any one of Aspects 24 through 32 wherein said amount of said replacement fluid/therapeutic agent delivered is a fraction of a total amount of therapeutic agent to be delivered to said subject.

Aspect 34. The method of Aspect 33 comprising pausing said delivery of said replacement fluid/therapeutic agent.

Aspect 35. The method of any one of Aspects 24 through 34 further comprising delivering an amount of a volume replacement fluid to said subject.

Aspect 36. The method of Aspect 35 comprising delivering said therapeutic agent separately from delivering said volume replacement fluid.

Aspect 37. The method of any one of Aspects 35 through 36 comprising monitoring the amount of volume replacement fluid delivered to the subject.

Aspect 38. The method of any one of Aspects 9 and 24 through 37, wherein said fluid circuit includes a reservoir in flow communication with an outlet on said separator, said method further comprising delivering separated formed components to said reservoir.

Aspect 39. The method of Aspect 38 further comprising reinfusing said formed components to said patient through said venipuncture needle.

Aspect 40. The method of Aspect 39 comprising withdrawing said whole blood and reinfusing said formed components in repeating cycles.

Aspect 41. The method of Aspect 40 further comprising delivering said replacement fluid/therapeutic agent after a final cycle.

Aspect 42. The method of any one of Aspects 9 and 24 through 37 wherein said fluid circuit comprises a first venipuncture needle and a second venipuncture needle, said method comprising withdrawing said whole blood through said first venipuncture needle and reinfusing said formed components through said second venipuncture needle.

Aspect 43. The method of Aspect 42 further comprising delivering said replacement fluid/therapeutic agent through said second venipuncture needle after said reinfusing of said formed components.

It will be understood that the embodiments described are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope of the claims is not limited to the above-description, but is set forth in the following claims.

The invention claimed is:

1. A plasmapheresis system for performing a therapeutic plasma exchange comprising a reusable hardware component and a disposable fluid circuit:
   a) the disposable fluid circuit comprising i) a separator for separating whole blood into a plasma fraction and a formed component fraction, the separator having an input having a blood line integrally connected thereto for transporting whole blood from a subject to the separator, a plasma output port integrally connected to a plasma collection container by a plasma line, and a formed component outlet port; ii) said blood line terminating in a venipuncture needle for transporting whole blood from a subject to the blood line, iii) an anticoagulant line integrally connected to the blood line and configured to be connected to a source of anticoagulant for transporting anticoagulant to the blood line, iv) a fluid replacement line configured for delivering a replacement fluid/therapeutic agent to the subject, v) a reinfusion line for transporting formed components to said subject; vi) a container of volume replacement fluid and a container of a therapeutic agent wherein said container of volume replacement fluid and said container of said therapeutic agent are in openable flow communication with said replacement fluid line, and vii) one or more flow controllers for establishing flow of said volume replacement fluid through said fluid replacement line while preventing flow of said therapeutic agent through said fluid replacement line,
   b) the reusable hardware component comprising a plurality of pumps for delivering anticoagulant at a controlled rate into the blood line during a collection phase, anticoagulated whole blood to the separator during the collection phase and for returning concentrated cellular components during a reinfusion phase, concentrated cellular components from the separator and infusing a replacement fluid/therapeutic agent and a programmable controller configured to:
      i. monitor separated plasma collected and pause or terminate collection when a predetermined amount of plasma has been collected;
      ii. initiate the reinfusion of said concentrated cellular components to said subject,
      iii. initiate delivery of a predetermined amount of a replacement fluid/therapeutic agent through the fluid replacement line from a source after collecting said predetermined amount of plasma and after said reinfusion and
      iv. selectively allow and block flow from both said container of volume replacement fluid and said container of a therapeutic agent to infuse said treating agent at one point of said therapeutic plasma exchange procedure and to infuse a volume replacement fluid at another point of said therapeutic plasma exchange procedure.

2. The system of claim 1 wherein said therapeutic agent comprises albumin.

3. The system of claim 1 wherein said fluid circuit further comprises a reservoir integrally connected to said formed component outlet port of said separator.

4. The system of claim 1 wherein said disposable fluid circuit comprises a first venipuncture needle for transporting whole blood from a subject and a second venipuncture needle for returning said formed components and delivering said replacement fluid/therapeutic agent to said subject.

5. The system of claim 4 wherein said fluid replacement line is in flow communication with said second venipuncture needle.

6. The system of claim 1 wherein hardware component comprises one or more weigh scales is configured to receive a source of replacement fluid/therapeutic agent.

7. The system of claim 6 wherein said reinfusion line is in flow communication with said blood line and said venipuncture needle.

8. The system of claim 1 wherein said fluid replacement line is in openable flow communication with said reinfusion line.

9. The system of claim 1 wherein said controller is further configured to monitor amount of said replacement fluid/therapeutic agent delivered to said subject.

10. The system of claim 1 further comprising a sensor that sends a signal to the controller when a predetermined amount of said replacement fluid/therapeutic agent has been delivered to said subject.

11. The system of claim 1 wherein said controller is further configured to calculate an amount of replacement fluid/therapeutic agent delivered to said subject wherein said amount of therapeutic agent delivered is based on a percentage of collected plasma.

12. The system of claim 11 wherein said controller is further configured to pause or terminate said delivery of said therapeutic agent when said amount of replacement fluid/therapeutic agent based on said a ratio of collected plasma/therapeutic agent is delivered to said subject.

13. The system of claim 1 wherein said amount of said replacement fluid/therapeutic agent is a fraction of a total volume of said therapeutic agent to be delivered and said controller is further configured to pause said delivery of said therapeutic agent when said fraction has been delivered to said subject.

14. The system of claim 1 wherein said one or more flow controllers comprises a three-way valve.

15. The system of claim 1 wherein said controller is configured to calculate a target volume of plasma to be collected based on at least two of the height, weight, sex, age and hematocrit of said subject.

16. The system of claim 15 wherein the controller is configured to calculate an amount of said replacement fluid/treating therapeutic agent to be delivered based on said calculated target volume of plasma to be collected.

17. The system of claim 1 comprising a reservoir in flow communication with a second outlet on said separator for receiving the separated formed components.

18. The system of claim 1 wherein said disposable fluid circuit comprises a first venipuncture needle for transporting whole blood from a subject and a second venipuncture needle for returning said formed components and delivering said replacement fluid/therapeutic agent to said subject.

* * * * *